United States Patent [19]

Bohm et al.

[11] Patent Number: 4,948,586

[45] Date of Patent: Aug. 14, 1990

[54] MICROENCAPSULATED INSECTICIDAL PATHOGENS

[75] Inventors: Howard A. Bohm; Deborah R. Friend, both of Richmond, Va.

[73] Assignee: Lim Technology Laboratories, Inc., Richmond, Va.

[21] Appl. No.: 233,522

[22] Filed: Aug. 18, 1988

Related U.S. Application Data

[63] Continuation-in-part of Ser. No. 115,879, Nov. 2, 1987, Pat. No. 4,844,896.

[51] Int. Cl.$^5$ .................... A61K 39/02; A61K 9/50
[52] U.S. Cl. .................... 424/406; 424/407; 424/408; 424/409; 424/417; 424/418; 424/419; 424/89; 424/91; 424/92
[58] Field of Search .............. 424/93, 408, 406, 409, 424/407, 417, 418, 419, 92, 91, 89, DIG. 10; 514/919

[56] References Cited

U.S. PATENT DOCUMENTS

| | | | |
|---|---|---|---|
| 2,090,109 | 8/1937 | Coe | 424/405 |
| 3,541,203 | 11/1970 | Fogle et al. | 424/464 |
| 3,641,237 | 2/1972 | Gould et al. | 424/487 X |
| 3,642,982 | 2/1972 | Morimoto et al. | 424/93 |
| 3,767,783 | 10/1973 | Sweeny et al. | 424/93 |
| 3,959,464 | 5/1976 | De Savigny | 424/78 |
| 3,966,902 | 6/1976 | Chromecek | 424/78 X |
| 4,001,480 | 1/1977 | Shank | 428/411 |
| 4,102,806 | 7/1978 | Kondo et al. | 424/93 X |
| 4,198,782 | 4/1980 | Kydonieus et al. | 424/419 X |
| 4,223,007 | 9/1980 | Spence et al. | 424/88 X |
| 4,321,117 | 3/1982 | Kaetsu et al. | 204/159.16 |
| 4,435,383 | 3/1984 | Wysong | 424/419 X |
| 4,436,719 | 3/1984 | Lindaberry | 424/419 X |
| 4,554,155 | 11/1985 | Allan et al. | 424/419 |
| 4,661,351 | 4/1987 | Gago et al. | 424/93 |
| 4,722,838 | 2/1988 | Tocker et al. | 424/81 X |
| 4,744,933 | 5/1988 | Rha | 424/93 X |
| 4,751,082 | 6/1988 | Schaerffenberg et al. | 424/93 |

FOREIGN PATENT DOCUMENTS

2939746 8/1980 Fed. Rep. of Germany.

OTHER PUBLICATIONS

Journal of Economic Entomology, vol. 59, No. 3, p. 620 "Encapsulation as a Technique for Formulating Microbial" Jun. 1966.
Journal of Economic Entomology, vol. 64, No. 4, p. 852 "Microencapsulation and Ultraviolet Protectants" Aug. 1971.

Primary Examiner—Thurman K. Page
Attorney, Agent, or Firm—Burns, Doane, Swecker & Mathis

[57] ABSTRACT

A microencapsulated insecticidal pathogen for application to vegetation is disclosed. An insecticidal viral, bacterial or fungal pathogen is encapsulated in a polymeric encapsulating agent such as Eudragit L, Eudragit S, Eudragit L or S with Eudragit RL, Eudragit L or S with Eudragit RS, polyacrylates, polyacrylic acids, cyclic acrylate polymer or mixtures thereof. Also encapsulated in the polymeric encapsulating agent is a sunscreening agent such as benzophenone, para amino benzoic acid, benzil, or mixtures thereof. Also disclosed is a process for encapsulating an insecticidal pathogen. The microcapsules of the invention effectively retain sunscreening agent within the capsule and are easily prepared without using toxic materials requiring subsequent removal.

13 Claims, No Drawings

MICROENCAPSULATED INSECTICIDAL PATHOGENS

The present application is a continuation-in-part of, U.S. Application Ser. No. 115,879 filed Nov. 2, 1987, U.S. Pat. No. 4,844,894.

BACKGROUND OF THE INVENTION

The present invention relates to biological insecticides and, more particularly, to novel microencapsulated insecticidal pathogens for application to vegetation.

Concern over the toxic side effects of chemical insecticides on man as well as on the environment has led to the development of biological insecticides and, more particularly, insecticidal bacteria, viruses and fungi. Such pathogens, while deadly if ingested by the target insects, are generally harmless to non-target insects as well as to man and other forms of wildlife. Thus, viruses are known which are effective against the bullworm *Heliothis zea* and the tobacco bullworm *H. virescens*, the gypsy moth *Lymantria dispar*, the Douglas fir tossock moth *Orgia pseudotsugata*, the European pine saw fly *Neodiprion sertifer* and both alfalfa and cabbage loopers *Autographa californica*.

Although viruses such as those described above as well as certain bacteria and fungi are highly effective against their target insects, their effectiveness is generally short-lived. More specifically, ultraviolet rays from the sun decrease the potency of the biological preparations thus necessitating virtually daily applications of the preparations to susceptible vegetation. Quite clearly, this need to repeatedly apply the insecticidal preparations substantially diminishes their cost effectiveness vis-a-vis conventional chemical insecticides which do not require so many repeated applications.

To prevent ultraviolet deactivation of insecticidal viruses, for example, formulations have been prepared containing both virus and a sunscreening agent. The presence of sunscreening agents does retard viral deactivation under laboratory conditions. However, results have been less than satisfactory when virus/sunscreening agent formulations were tested in the field. More specifically, when formulations containing both virus and sunscreening agent were dispersed in the field, the sunscreening agent was no longer in close enough contact to the virus to be effective at reducing the exposure of the viruses to the damaging effects of ultraviolet light.

Attempts have been made to provide formulations wherein an insecticidal virus and a sunscreening agent are maintained in close contact after dispersion of the formulation onto vegetation. Thus, C. M. Ignaffo and 0.F. Batzer described "Microencapsulation and Ultraviolet Protectants to Increase Sunlight Stability of an Insect Virus" in the *Journal of Economic Entomology*, Volume 64, Number 4, pp. 850–853, August 1971. Ignaffo et al attempted to use microencapsulation, as one of several ways, to increase the sunlight stability of the polyhedral inclusion bodies of the Heliothis nucleopolyhedrosis virus. Thus, samples of virus alone or virus and sunlight protectants were prepared for encapsulation. Among the sunlight protectants were Buffalo Black, Carbo-Jet Black, cellulose, carbon, aluminum powder and aluminum oxide. Among the microencapsulating walls were ethylcellulose and gelatin. Microcapsules containing virus and sunlight protectant were found to be more stable than virus alone. However, nonencapsulated mixtures of virus and sunlight protectant were found to be equally as: stable as the corresponding microencapsulated mixtures.

Since only laboratory tests are discussed by Ignoffo et al, it is not surprising that their conclusion was that nonencapsulated mixtures of virus and sunscreening agent were as stable as the corresponding microencapsulated mixtures. Nonetheless, it is quite clear that the microencapsulated formulations of Ignoffo et al are not suitable for application to fields. In the first place, encapsulating materials such as the ethylcellulose employed by Ignaffo et al are not sticky and thus, will readily fall off the leaves of the plants which they are supposed to protect from insecticidal damage. Another problem is that the encapsulating materials are not environmentally stable. For example, the gelatin coating used is readily broken down by the environment. Finally, some of the sunscreening agents, e.g., the carbon black, are not desirable in terms of their appearance.

Attempts have also been made to provide formulations wherein an insecticidal bacteria is microencapsulated. Thus, E.S. Raun and R. D. Jackson in "Encapsulation as a Technique for Formulating Microbial and Chemical Insecticides" in the *Journal of Economic Entomology*, Volume 59, Number 3, pp. 620–622 (1966) describe encapsulation of the bacterium *Bacillus thuringiensis* which is a pathogen of the European corn borer. The encapsulated bacteria were found to be as effective as standard clay granular formulations. The specific encapsulating agents are not discussed nor is the presence of a sunscreening agent disclosed. Accordingly, such formulation could be expected to suffer from a number of the disadvantages described above, i.e., ultraviolet breakdown of the pathogen, lack of stability in the field, inability to adhere to a treated plant and inability of the capsule to be broken down in the stomach of an insect.

More recently, Fogle et al in U.S. Pat. No. 3,541,203 developed a protected virus composition for insect control. The composition includes (1) a virus to be used as an insecticide, (2) protecting materials which aid in prevention of the deactivation of the viruses and which prolong the effectiveness of the virus, and (3) preferably a polymeric material to bind the light absorbing compound and the virus particles together as minute particles.

To maintain the virus composition, once applied, in the desired location on the leaves of plants, the sprayable composition includes, along with minute particles of the virus and light absorbing material in a binder, a liquid carrier vehicle which has dissolved therein a "sticker material". Where the polymeric binder material is substantially water-insoluble, the liquid vehicle is water or an aqueous solution and the sticker material is a water-soluble polymeric material such as methyl cellulose or polyvinyl alcohol. In another embodiment wherein the polymeric material is slightly water-soluble or water swellable, an aqueous vehicle need not include a sticker material because the polymeric material is slightly swollen by the aqueous vehicle and serves as its own sticker.

One suitable polymeric binding material is cellulose acetate phthalate which becomes soluble in water at a pH of about 7 and might more easily release the virus for use in infecting insects after being ingested by the insect. More specifically, cellulose acetate phthalate is believed to operate in an enteric fashion in the digestive tract of insect larvae wherein material in the digestive tract is alkaline.

To bind the admixture of sunscreening agent and virus together with an ethylcellulose polymeric material, Fogle et al combined the admixture with 2% ethylcellulose in toluene. While agitating the mixture, polybutadiene was added and the mixture poured into a vessel containing a petroleum distillate which caused the ethylcellulose to solidify to yield very small particles of ethylcellulose polymeric material having substantially homogeneously enclosed within the particles the admixture of carbon and polyhedrosis virus. It was then necessary to wash the capsules with additional petroleum distillate to completely remove residual amounts of the liquid polybutadiene material.

The microencapsulating process as well as the microcapsules obtained by Fogle et al suffer from a number of disadvantages. More specifically, the polymers forming the walls of the capsules are not always capable of retaining the sunscreening agent within the interior of the capsule. This of course diminishes the stability of the insecticidal preparation since the loss of sunscreening agent makes the pathogen more susceptible to the damaging effects of ultraviolet light. Another problem with the microcapsules of Fogle et al is that highly toxic materials are employed in their preparation and cumbersome washing steps are required for their removal.

SUMMARY AND OBJECTS OF THE INVENTION

In view of the foregoing limitations and shortcomings of prior art microencapsulated biological insecticides as well as other disadvantages not specifically mentioned above, it should be apparent that there still is a need in the art for a microencapsulated biological insecticide which effectively retains i&:s sunscreening agent and which can be prepared without using toxic materials which must subsequently be removed.

It is, therefore, a primary objective of the present invention to fulfill that need by providing a microencapsulated insecticidal pathogen formed from an acrylic based polymeric encapsulating agent and a sunscreening agent which is retained by the acrylic based polymeric encapsulating agent. It is also an object of the present invention to provide a microencapsulated insecticidal pathogen which can be prepared without toxic substances which must be removed by subsequent washing steps.

A further object of the present invention is to provide a microencapsulated pathogen in which a sunscreening agent is maintained in close enough contact with the pathogen to prevent degradation thereof by ultraviolet light.

Yet another object of the present invention is to provide a microencapsulated insecticidal pathogen which is generally soft and thus easily ingested by a target insect.

In a first aspect, the present invention relates to a microencapsulated pathogen comprising:

(i) an insecticidal pathogen;

(ii) a polymeric encapsulating agent comprising Eudragit L, Eudragit S, Eudragit RL, Eudragit RS, polyacrylates, polyacrylic acids, cyclic acrylate polymer or mixtures thereof;

(iii) a sunscreening agent comprising benzophenone, para amino benzoic acid, benzil or mixtures thereof.

In a second aspect, the present invention relates to a method for preparing a microencapsulated pathogen comprising the steps of:

(i) mixing (A) an encapsulating polymer comprising Eudragit L, Eudragit S, Eudragit L or S with Eudragit RL, Eudragit I, or S with Eudragit RS, polyacrylates, polyacrylic acid, or cyclic acrylate polymer, (B) a sunscreening agent comprising benzophenone, para amino benzoic acid, benzil or mixtures thereof and (C) a solvent comprising at least one of polyethylene glycol, propylene glycol, a methylene chloride and propylene glycol mixture, tetrahydrofuran, tetrahydropyran, furan, and pyran; the encapsulating polymer, sunscreening agent, and solvent forming a first solution;

(ii) preparing an aqueous suspension of the insecticidal pathogens;

(iii) preparing a second aqueous surfactant solution having a pH below 7; and (iv) mixing said first solution, said aqueous suspension, and said second aqueous surfactant solutions to form microcapsules.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF PREFERRED EMBODIMENTS

A. Starting materials

The basic starting materials for preparing the microencapsulated pathogens according to the present invention are the insecticidal virus, bacterium, or fungi; the polymer used to encapsulate the pathogen; and the sunscreening agent.

The invention is not limited to any particular insecticidal pathogen. Thus, any of the pathogens currently known to infect insects, including viral, bacterial and fungal pathogens, can be encapsulated and protected from ultraviolet light with a sunscreening agent. One class of viral pathogens which have been found to have considerable potential as biological insecticides are the nuclear polyhedrosis viruses which are classified in the family Bacculoviradie. Four such viruses which have been registered with the Environmental Protection Agency for commercial use are the nuclear polyhedrosis virus (hereinafter referred to as NPV) of the bullworm *Heliothis zea,* for the control of the bullworm and the tobacco bullworm, *H. virescens,* the NPV of the gypsy moth *Lymantria dispar,* for the control of gypsy moth, the NPV of the Douglas fir tossock moth, *Orgia pseudotsugata* for the control of the Douglas fir tossock moth, the NPV of the European pine saw fly *Neodiprion sertifer.* The NPV of *Autographa californica* which infects both alfalfa loopers and cabbage loopers has been submitted to the Environmental Protection Agency for approval. The invention, of course, is not limited to the above viruses but rather encompasses any of insecticidal viruses which remain viable at a pH of less than about 7.

Any of the bacterium known to be pathogenic to target insects may also be encapsulated according to the present invention. Exemplary bacteria include *Bacillus thuringiensis* which is effective against the European corn borer.

As previously discussed, the polymers employed to encapsulate the viruses or bacteria should exhibit certain properties:. In the first place, the polymers should be capable of retaining the sunscreening agent within the microcapsule. Additionally, the polymers should be insoluble in the environment to which the treated vegetation is exposed. Generally, such environments are slightly acidic, i.e., at a pH level below about 7. Additionally, the polymers should be soluble in the environment of an insect's stomach, i.e., at alkaline pH levels above about 7 so that the virus or bacterium can be released to infect the target insect. Another property required of the encapsulating polymer is that it should be capable of sticking to the vegetation to which it is applied. Without such stickiness, the microcapsules will tend to fall off the vegetation and will therefore not be ingested by insects feeding on the vegetation.

Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. A particularly preferred group of encapsulating polymers are the polyacrylic acids Eudragit L and Eudragit S which optionally may be combined with Eudragit RL or RS. These modified acrylic acids are useful since they can be made soluble at a pH of 6 or 7.5, depending on the particular Eudragit chosen, and on the proportion of Eudragit S to Eudragit L, RS, and RL used in the formulation. By combining one or both of Eudragit L and Eudragit S with Eudragit RL and RS (5–25%), it is possible to obtain a stronger capsule wall and still retain the capsule's pH-dependent solubility.

The sunscreening agents employed are those which, in addition to blocking out ultraviolet light, are compatible with the encapsulating polymer and the insecticidal pathogen. One criterion of compatibility between the encapsulating polymer and the sunscreening agent is that the encapsulating polymer be capable of retaining the sunscreening agent within the capsule.

A number of dyes have been found by the present inventors to be useful as the sunscreening agents for the microcapsules of the present invention. Such dyes include methyl orange, malachite green and its hydrochloride, methyl green, brilliant green, an FDC green, coomasie brilliant blue R, methylene blue HCl salt, brilliant cresyl blue, acridine yellow, an FDC yellow, an FDC red, and fluorescein free acid. According to the present invention, the sunscreening agents include benzophenone, para amino benzoic acid, benzil or mixtures thereof.

A number of conventional additives may also be incorporated into the microcapsules of the present invention. Such additives include, but are not limited to stabilizers, preservatives, anti-fungal agents, anti-mold agents and anti-bacterial agents. Quite clearly, anti-bacterial agents generally would not be employed when bacterial pathogens are encapsulated.

B. Preparation of Microcapsules

A number of schemes for preparing microencapsulated viruses are now described. It will be appreciated that such techniques: are also applicable to the encapsulation of insecticidal bacteria and fungi. Unless indicated otherwise, all percentages reported are by weight.

To prepare the microencapsulated viruses of the present invention, about 1.0 to about 4.0 g of the encapsulating polymer are dissolved in polyethylene glycol or another suitable solvent such as pyran, propylene glycol, a methylene chloride and propylene glycol mixture, furan, tetrahydrofuran or tetrahydropyran. The polyethylene glycol preferably has a molecular weight ranging from about 200 to about 400. To reduce the tackiness of the drying lacquer, 0.05 to 0.10 g of a glidant such as magnesium stearate can be added. Although magnesium stearate is preferred, other glidants can be employed such as talc, calcium stearate and calcium sulfate. In a preferred embodiment, 1.0 to 2.0 g of the encapsulating polymer are initially dispersed in 5 ml of solvent followed by the addition of 10 to 15 ml of additional solvent to dissolve all of the encapsulating polymer. To the solution of the encapsulating polymer is then added enough sunscreening agent to form a 0.1 to 0.5% by weight solution of sunscreening agent.

An aqueous suspension of the insecticidal pathogen is next prepared. Generally, stock samples of the pathogen which are readily available or easily prepared, are diluted to the desired concentration. The concentration of the viral, bacterial or fungal suspension, of course, depends on the amounts of such pathogens required to kill or at least repel the target insects. Such concentrations are readily ascertained by persons skilled in the art. In terms of the relative amounts of aqueous suspension and polymeric solution employed, persons in the art further appreciate that there must be sufficient water to suspend the amounts of pathogen required but not so much as to cause the encapsulating polymer to precipitate out when combined with the aqueous suspension. Generally, 15–25 ml of the encapsulating polymer and 0.037 to 0.047 g of sunscreening agent are present per 20 ml of virus after the two solutions have been combined.

The aqueous suspension of virus is then emulsified with the solution containing the encapsulating polymer and the sunscreening agent to form a first emulsion.

The above ranges are merely exemplary. Thus, persons skilled in the art of microencapsulation will appreciate that suitable microcapsules can be formed from a relatively wide range of concentrations of ingredients.

A second aqueous solution is then prepared by mixing conventional surfactants with distilled water such that a 8.5 to 12.5% aqueous surfactant solution results. While the invention is not limited to any particular surfactant, a surfactant having an HLB range of from about 1.8 to about 5.0 is preferred. In this regard, span 80 and span 85 are preferred. In order to form the aqueous surfactant solution, it may be necessary to heat it slightly while stirring. Sunscreening agent may then be added to the aqueous surfactant solution such that the concentration of the sunscreening agent therein ranges from 0.1 to 0.50%. The aqueous surfactant solution is then combined with the previously prepared first emulsion to produce a second emulsion leading to the formation of microcapsules containing the virus and the sunscreening agent. The relative amounts of the second aqueous surfactant solution, the first solution and the pathogen suspension are chosen such that microcapsules will form. Thus, as is known in the encapsulating art, the amount of water that is used in the second aqueous solution should be more than is necessary to precipitate the polymeric mixture and allow the capsule to form. When mixing the various suspensions and solutions, non-aerated stirring is preferably employed since such technique rapidly diffuses solvents such as polyethylene glycol, avoids the formation of large globs, and prevents incorporation of air in&:o the capsules.

In a second preferred embodiment for forming the microcapsules of the invention, the sunscreening agent is not present in either the first or second emulsions. Rather, the sunscreening agent is added to the microcapsules after they have formed by combining the sunscreening agent in fine powder form with the microcapsules such that the sunscreening agent comprises 0.10 to 0.50% of the total volume.

In a third preferred embodiment for preparing the microencapsules of the invention, a solution is prepared by mixing an organic solvent such as ethanol with deionized water, preferably in a 60:40 ethanol: water ratio. To the aqueous ethanol is then added between about 2.5 and 3.5 parts by weight of the encapsulating polymer. All of the above ingredients are heated until a solution forms. After allowing the solution to cool to room temperature, there are added to the solution surfactant, pathogen and sunscreening agent. Generally, 1.0 part by weight if surfactant and 0.1 to 0.5 parts by weight if sunscreening agent are employed. The amount of pathogen depends on the particular pathogen chosen and is readily ascertained by persons skilled in the art. The solution is then spray dried on a Buchi 190 mini spray dryer to yield fine capsules having a diameter ranging between 5 and 50 microns. The capsules resuspend easily in water and, once reconstituted, can be used directly.

Without being limited to theory, it is believed that the microcapsules formed in accordance with the present invention are analogous to gelatin balls having a hard coating which progressively becomes softer towards the center. Thus, the insecticidal pathogens are located in a gelatinous material which is soft, viscous and composed of water, polymer and sunscreening agent.

C. Application of the Microcapsules to Vegetation

The microcapsules prepared by any of the above-described methods can generally be applied anywhere a conventional insecticide could be applied. Generally, the concentration of the microcapsules and the rate of application depend on the nature of the pathogen and on the nature of the vegetation being treated. Such are readily ascertainable by persons skilled in the art.

The following examples are presented in order to more fully illustrate the preferred embodiments of the invention. They should in no way be construed, however, as limiting the broad scope of the invention.

EXAMPLE 1

A polymeric solution was prepared by mixing about 1.8g of Eudragit S-100, about 0.1g of magnesium stearate and 5ml of polyethylene glycol (MW 400), and the mixture was stirred until all the solids were well dispersed in the polyethylene glycol. About 10ml of additional polYethylene glycol was added to the solution and the contents were stirred until all Eudragit S-100 dissolved. About 0.0369g of malachite green hydrochloride was added to this solution so that the weight of malachite green hydrochloride is 0.1% of the weight of the subsequent solution. An aqueous solution was prepared by diluting stock samples of the *Autographa californica* NPV to the desired concentrations. The polymeric solution and the aqueous solution were then emulsified to produce a first emulsion. A second aqueous solution was prepared by mixing about 4.25g of Span 80 and about 8.25g of span 85 and about 100g of distilled water. The solution was heated and stirred until the surfactants dissolved. About 0.1125g of malachite green hydrochloride was added to this solution to equal 0.1% of the solution volume. This solution was combined with the first solution and emulsified to produce a second emulsion slowly leading to microcapsules with virus and malachite green hydrochloride entrapped in the capsules. This sample and a sample prepared in exactly the same way were exposed to sunlight for 24 hours (equivalent to one week of sunlight). The sample with sunscreening agent retained 71.43% of its potency as compared with samples not exposed to sunlight. The formulations were also found to be quite sticky when the sprayed formulations dried.

EXAMPLE 2

An emulsion was prepared as above except without malachite green hydrochloride in the internal wall. Malachite green hydrochloride was added as a fine powder at the end of the reaction to a total of 0.1% of the total volume. This sample retained 33.3% of its potency after 24 hours exposure to sunlight as compared with an unexposed sample. The sprayed samples were sticky when dried.

EXAMPLE 3

An emulsion was prepared as above except that methyl green was used instead of malachite green hydrochloride. This sample retained 53.8% of its activity after 24 hours exposure to sunlight as compared with the unexposed sample. The sprayed samples were sticky when dried.

EXAMPLE 4

An emulsion was prepared as above except that methyl orange was used instead of malachite green hydrochloride or methyl green. The sunscreening agent was both inside and outside the capsule walls. The total concentration of the methyl orange was 0.1% by volume. The sample retained 30.7% of its activity after 24 hours exposure to sunlight as compared with the unexposed sample. The dried sprayed formulation was sticky.

EXAMPLE 5

A polymeric solution was prepared by mixing about 20g methylene chloride, about 0.1g magnesium stearate, about 1.8g Eudragit S-100, and about 10ml of polypropylene glycol MW 400. The mixture was stirred until all Eudragit S-100 dissolved.

An aqueous solution was prepared by diluting stock samples of the *Autographa californica* NPV to the desired concentrations. The polymeric solution and the aqueous solution were then emulsified to produce a first emulsion.

A second aqueous solution was prepared by mixing about 4.25g Span 80 and about 8.25g of Span 85 and about 100g of distilled water. This solution was combined with the first solution and emulsified to produce a second emulsion. The methylene chloride was then evaporated off by stirring and heating at approximately 45° C.

EXAMPLE 6

The procedure is the same as for the previous Example except that the Eudragit S-100 was dissolved in about 20 ml of polypropylene glycol.

EXAMPLES 7-10

Microcapsules were prepared using *A. californica* as the virus, Eudragit S-100 as the encapsulating polymer and malachite green, methyl green or methyl orange as the sunscreening agent. The precise capsule formulations and the effect of sunlight in the prepared capsules are set forth in Table I as follows:

TABLE I
REDUCTION IN ACTIVITY OF MICROENCAPSULATED VIRUS AFTER 24 HOUR EXPOSURE TO SUNLIGHT

| EXAMPLE | EUDRAGIT S-1000 | SOLVENT PEG 400 | AMT. VIRUS ENCAPSULATED | SPAN 80 | SPAN 85 | SUNSCREEN |
|---|---|---|---|---|---|---|
| 7 | 1.20% | 10.0% | 13.4% | 2.8% | 5.5% | 0.1% malachite green |
| 8 | 1.8 g 1.20% | 15 ml 10.0% | 20 ml 13.4% | 4.25 g 2.8% | 8.25 g 5.5% | 0.149 g methyl green 0.1% (based on weight 68.9 g) |
| 9 | 0.9 g 1.20% | 7.5 ml 10.1% | 10 ml 13.4% | 2.12 g 2.8% | 4.12 g 5.5% | 0.0689 g malachite green 0.1% (based on final weight 65.3 g.) |
| 10 | 0.9 g 1.20% | 7.5 ml 10.0% | 10 ml 13.4% | 2.12 g 2.8% | 4.12 g 5.5% | 0.0652 g methyl orange 0.1% |
| | 1.80 g | 15 ml | 20 ml | 4.25 g | 8.25 g | 0.149 g |

RESULTS 0.036 g malachite green added to wall material and 0.1125 g malachite green added to outer $H_2O$ layer before sample made. Sample retained 71.43% activity after being exposed to sunlight.

Sample was made without dye, then 0.0689 g methyl green was added to outer $H_2O$ layer to equal 0.1% sample volume (sample weight 68.9 g). Sample retained 58.3% activity after being exposed to sunlight.

Sample made same as Example 8. 0.0652 g malachite green added to outer $H_2O$ layer to equal 0.1% conc. (Sample weight 65.3 g.) Sample retained 33.3% activity after being exposed to sunlight.

0.0369 methyl orange added to wall material and 0.1125 g methyl orange added to outer $H_2O$ layer before sample was made. Sample retained 30.7% activity after being exposed to sunlight.

EXAMPLE 11

An organic solution was prepared by mixing 60 parts of absolute ethanol with 40 parts deionized water. To this was added about 3.0 g of Eudragit S-100 and the contents were heated and stirred until solution was complete. The solution was allowed to cool to room temperature and about 1.0 g of span 2.0, 1.0 ml of the required virus sample and 0.1 g of malachite green hydrochloride were added. The solution was sprayed on a Buchi 190 mini spray dryer yielding fine capsules of 5–50 micron diameter. The capsules re-suspend easily in water and can be used directly in their reconstituted form.

EXAMPLE 12

A polymeric solution was prepared by mixing about 1.8g of Eudragit S-100, about 0.1g magnesium stearate and 5ml of polyethylene glycol (mw400), and the mixture was stirred until all the solids were well dispersed in the polyethylene glycol. About 10ml of additional polyethylene glycol was added to the solution and the contents were stirred until all Eudragit S-100 dissolved. About 0.1143g Benzophenone was added to this solution &:o equal about 0.49% by weight of the first emulsion.

A first aqueous solution was prepared by concentrating stock samples of the *Bacillus thuringiensis* to the desired concentration, (in this case $1.68 \times 10$ spores plus crystals were concentrated down to a volume of 5ml). The polymeric solution and the aqueous solution were then emulsified to produce a first emulsion.

A second aqueous solution was prepared by mixing about 4.25g of Span 80 and about 8.25g of Span 85 and about 100g of distilled water. The solution was heated and stirred until the surfactants dissolved. This solution was combined with the first emulsion and emulsified to produce a second emulsion slowly leading to formulation of microcapsules.

EXAMPLE 13

An emulsion was prepared in the same manner as in Example 12 except 0.1160g Benzil wa added to the polymeric solution (internal wall). The concentration and volume of the aqueous *Bacillus thuringiensis* suspension was the same. The amount of Benzil in the wall was 0.5%.

EXAMPLE 14

An emulsion was prepared in the same manner as in Example 12 except 0.17g PABA (p-Aminobenzoic Acid) was added to the polymeric solution (internal wall). The concentration and volume of the aqueous *Bacillus thuringiensis* suspension was the same. The amount of PABA in the wall was 0.77%.

EXAMPLE 15

An emulsion was prepared in the same manner as in Example 12 except 0.023g methyl green was added to the polymeric solution (internal wall), and 0.1125g of methyl green was added to the second aqueous solution (aqueous surfactant solution). The concentration and volume of the aqueous *Bacillus thuringiensis* suspension was the same.

EXAMPLES 16–19

Microencapsulated virus samples were prepared following the procedures of Examples 12–14 by substituting the appropriate concentration of virus for bacteria, and using the indicated amount of sunscreen agent in each example.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. Microencapsulated pathogen comprising:
   (i) an insecticidal pathogen;
   (ii) a polymeric encapsulating agent comprising polyacrylates, polyacrylic acids, cyclic acrylate polymer, polyacrylamides or mixtures thereof;
   (iii) a sunscreening agent selected from the group consisting essentially of benzophenone, para aminobenzoic acid, benzil or mixtures thereof.

2. The microencapsulated pathogen of claim 1 wherein said insecticidal pathogen is a virus.

3. The microencapsulated pathogen of claim 2 wherein said virus is a nuclear polyhedrosis virus.

4. The microencapsulated pathogen of claim 1 wherein said polymeric encapsulating agent is based on methylacrylic acid and methylacrylic acid methyl ester wherein the ratio of free carboxyl groups to ester groups is about 1:1 or about 1:2, or copolymer synthesized from acrylic and methylacrylic acid esters with a low content of quaternary ammonium groups, wherein said copolymer has a molar ratio of ammonium groups to neutral methylacrylic or acrylic acid esters of about 1:10 or about 1:40.

5. The microencapsulated pathogen of claim 1 wherein said pathogen is *Bacillus thurigiensis.*

6. The microencapsulated pathogen of claim 5 wherein said pathogen is a nuclear polyhedrosis virus of *Heliothis zea, H. virescens, Lymantria dispar, Orgia pseudotsugata, Neodiprion sertifer,* or *Autographa californica.*

7. A process for encapsulating an insecticidal pathogen comprising the steps of:
   (i) mixing (A) an encapsulating polymer comprising at least one of polyacrylates, polyacrylamides (B) a sunscreening agent selected from the group consisting essentially of benzophenone, para aminobenzoic acid, benzil or mixtures thereof, and (C) a solvent comprising at least one of polyethylene glycol, propylene glycol, a mixture of methylene and propylene glycol, tetrahydrofuran, tetrahydropyran, furan, and pyran; said encapsulating polymer, sunscreening agent and solvent forming a first solution;
   (ii) preparing an aqueous suspension of the insecticidal pathogen;
   (iii) preparing a second aqueous surfactant solution having a pH below 7; and
   (iv) mixing said first solution, said aqueous suspension, and said second aqueous surfactant solutions to form microcapsules.

8. The process of claim 7 wherein said polymeric encapsulating agent is based on methylacrylic acid and methylacrylic methyl ester wherein the ratio of free carboxyl groups to esters groups is about 1:1 or about 1:2 or copolymer synthesized from acrylic and methylacrylic acid esters with a low content of quaternary ammonium groups, wherein said copolymer has a molar ratio of ammonium groups to neutral methylacrylic or acrylic acid esters of about 1:10 or about 1:40.

9. The process of claim 7 wherein said solvent is polyethylene glycol.

10. The process of claim 9 wherein said polyethylene glycol has a molecular weight ranging from about 200 to about 400.

11. The process of claim 7 wherein the pH of said second aqueous surfactant solution is below 6.

12. The process of claim 7 wherein said aqueous surfactant solution is non-ionic.

13. The process of claim 12 wherein said aqueous surfactant solution is prepared from a surfactant having an HLB range of from about 1.8 to about 5.0.

* * * * *